(12) United States Patent
Schmitt et al.

(10) Patent No.: US 12,290,579 B2
(45) Date of Patent: *May 6, 2025

(54) EFFECT PIGMENTS HAVING A REFLECTIVE CORE AND SEMICONDUCTOR LAYERS

(71) Applicant: ECKART AMERICA CORPORATION, Painesville, OH (US)

(72) Inventors: Devin Schmitt, Munster, IN (US); Jonglak Choi, Munster, IN (US)

(73) Assignee: ECKART AMERICA CORPORATION, Painesville, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/720,721

(22) PCT Filed: Dec. 6, 2022

(86) PCT No.: PCT/IB2022/061830
§ 371 (c)(1),
(2) Date: Jun. 17, 2024

(87) PCT Pub. No.: WO2023/119035
PCT Pub. Date: Jun. 29, 2023

(65) Prior Publication Data
US 2025/0049650 A1    Feb. 13, 2025

(30) Foreign Application Priority Data

Dec. 22, 2021    (EP) .................................. 21216793

(51) Int. Cl.
| | | |
|---|---|---|
| A61K 8/02 | (2006.01) | |
| A61K 8/25 | (2006.01) | |
| A61K 8/26 | (2006.01) | |
| C09C 1/00 | (2006.01) | |
| C09C 1/64 | (2006.01) | |

(52) U.S. Cl.
CPC .............. *A61K 8/0262* (2013.01); *A61K 8/25* (2013.01); *A61K 8/26* (2013.01); *C09C 1/0021* (2013.01); *C09C 1/642* (2013.01); *C09C 2200/107* (2013.01); *C09C 2200/301* (2013.01); *C09C 2200/302* (2013.01); *C09C 2200/401* (2013.01); *C09C 2200/407* (2013.01)

(58) Field of Classification Search
CPC .................................................... A61K 8/0262
See application file for complete search history.

(56) References Cited

U.S. PATENT DOCUMENTS

| | | |
|---|---|---|
| 4,011,190 A | 3/1977 | Telkes |
| 4,268,541 A | 5/1981 | Ikeda |
| 5,624,076 A | 4/1997 | Miekka |
| 5,629,068 A | 5/1997 | Miekka |
| 5,672,410 A | 9/1997 | Miekka |
| 5,766,335 A | 6/1998 | Bujard |
| 5,795,649 A | 8/1998 | Cosentino |
| 5,874,167 A | 2/1999 | Rawlings |
| 6,013,370 A | 1/2000 | Coulter |
| 6,068,691 A | 5/2000 | Miekka |
| 6,200,399 B1 | 3/2001 | Thielman |
| 6,333,053 B1 | 12/2001 | Simon |
| 6,692,830 B2 | 2/2004 | Argoitia |
| 6,761,762 B1 | 7/2004 | Greiwe |
| 8,197,591 B2 * | 6/2012 | Kaupp .................. C09C 1/0015 106/490 |
| 8,851,649 B2 * | 10/2014 | Engel .................. C09D 11/322 347/100 |
| 9,000,068 B2 * | 4/2015 | Trummer .................. C09C 1/22 524/439 |
| 9,453,131 B2 | 9/2016 | Geissler |
| 9,624,378 B2 | 4/2017 | Hippman |
| 10,443,808 B1 | 10/2019 | Heib |
| 10,557,037 B2 | 2/2020 | Kreppner |
| 11,617,707 B2 | 4/2023 | Schilling |
| 2002/0041047 A1 | 4/2002 | Josephy |

(Continued)

FOREIGN PATENT DOCUMENTS

| | | |
|---|---|---|
| CN | 201432443 | 3/2010 |
| CN | 105086627 A | 11/2015 |

(Continued)

OTHER PUBLICATIONS

International Preliminary Report on Patentability for International Application No. PCT/IB2022/061830 mailed Feb. 2, 2024.
International Search Report and Written Opinion for International Application No. PCT/IB2022/061830 mailed Feb. 14, 2023.
L. Jin et al., "Large area Germanium Tin nanometer optical film coatings on highly flexible aluminum substrates," Scientific Report, May 16, 2016, pp. 1-6.
M. A. Kats, R. Blanchard, P. Genevet, and F. Capasso, "Nanometre optical coatings based on strong interference in highly absorbing media," Nat. Mater. 12(1), 20-24 (2012).
P. Moontragoon et al., "Band strcutre calculations of Si—GE—Sn alloys: achieving direct band gap materials," Semicon. Sci. Technol. 22 (207) 742-748.

(Continued)

*Primary Examiner* — Gina C Justice

(57) ABSTRACT

Disclosed herein is an effect pigment having a layer stack which comprises a highly reflective metallic flake having a first major interface and opposed to this first interface a second major interface, and at least one side surface and directly adjacent on one or of both of these major interfaces a layer of a semiconducting material having an average atomic composition of:

a) $Si_{(1-x)}Sn_x$, wherein $0<x<0.90$ or
b) $Ge_{(1-y)}Sn_y$, wherein $0<y\leq0.80$ or
c) $Si_{(1-m-n)}Ge_mSn_n$, wherein $0<m<1.00$, $0<n<1.00$ and with the proviso that $m+n<1.00$.

19 Claims, No Drawings

(56) References Cited

U.S. PATENT DOCUMENTS

| | | |
|---|---|---|
| 2003/0031870 A1 | 2/2003 | Argoitia |
| 2003/0104206 A1 | 6/2003 | Argoitia |
| 2003/0190473 A1 | 10/2003 | Argoitia |
| 2003/0224164 A1 | 12/2003 | Argoitia |
| 2004/0076819 A1 | 4/2004 | Pitt |
| 2004/0081807 A1 | 4/2004 | Bonkowski |
| 2004/0131776 A1 | 7/2004 | Weinert |
| 2005/0120917 A1 | 6/2005 | Ruger |
| 2006/0077496 A1 | 4/2006 | Argoitia |
| 2006/0105196 A1 | 5/2006 | Roth |
| 2007/0139744 A1 | 6/2007 | Argoitia |
| 2007/0199478 A1 | 8/2007 | Schlegl |
| 2007/0207099 A1 | 9/2007 | Erker |
| 2008/0207772 A1 | 8/2008 | Kniess |
| 2008/0274354 A1 | 11/2008 | Rettker |
| 2009/0174944 A1 | 7/2009 | Yuasa |
| 2009/0274960 A1 | 11/2009 | Yokouchi |
| 2010/0022696 A1 | 1/2010 | Maruoka |
| 2010/0060987 A1 | 3/2010 | Witzman |
| 2010/0062244 A1 | 3/2010 | Bujard |
| 2010/0207842 A1 | 8/2010 | Kawaguchi |
| 2010/0242793 A1 | 9/2010 | Greb |
| 2010/0272932 A1 | 10/2010 | Izumo |
| 2011/0008399 A1 | 1/2011 | Bugnon |
| 2011/0031640 A1 | 2/2011 | Josephy |
| 2012/0100364 A1 | 4/2012 | Yoon |
| 2012/0113517 A1 | 5/2012 | Yuasa |
| 2012/0114920 A1 | 5/2012 | Yoon |
| 2013/0045338 A1 | 2/2013 | Argoitia |
| 2013/0068410 A1 | 3/2013 | Donohue |
| 2013/0192789 A1 | 8/2013 | Rettker |
| 2013/0209790 A1 | 8/2013 | Geissler |
| 2013/0285362 A1 | 10/2013 | Witzman |
| 2013/0288024 A1 | 10/2013 | Clauter |
| 2013/0300008 A1 | 11/2013 | Yuasa |
| 2014/0049427 A1 | 2/2014 | Keckes |
| 2014/0154520 A1 | 6/2014 | Rettker |
| 2014/0368918 A1 | 12/2014 | Banerjee |
| 2015/0296936 A1 | 10/2015 | Demange |
| 2015/0309231 A1 | 10/2015 | Banerjee |
| 2016/0145438 A1 | 5/2016 | Ponce |
| 2017/0133669 A1 | 5/2017 | Green |
| 2017/0168137 A1 | 6/2017 | Cho |
| 2017/0306158 A1 | 10/2017 | Argoitia |
| 2021/0078870 A1 | 3/2021 | Zamora Abanades |
| 2021/0292568 A1 | 9/2021 | Ma |

FOREIGN PATENT DOCUMENTS

| | | |
|---|---|---|
| CN | 106433323 A | 2/2017 |
| DE | 102006027134 A1 | 1/2007 |
| DE | 102009025950 | 12/2010 |
| DE | 102011088154 A1 | 6/2013 |
| EP | 1463631 | 10/2004 |
| EP | 3269780 | 1/2018 |
| EP | 3403824 A1 | 11/2018 |
| JP | H11152437 A | 6/1999 |
| JP | 2005298907 | 10/2005 |
| JP | 2007286113 | 11/2007 |
| JP | 2011029548 | 2/2011 |
| JP | 2013118405 | 6/2013 |
| JP | 2015096628 | 5/2015 |
| KR | 20170047070 | 5/2017 |
| WO | 1993023481 | 11/1993 |
| WO | 1999035194 | 7/1999 |
| WO | 2000031571 | 6/2000 |
| WO | 2001053113 | 7/2001 |
| WO | 20002024818 | 3/2002 |
| WO | 2002040599 | 5/2002 |
| WO | 2002040600 | 5/2002 |
| WO | 2003064543 | 8/2003 |
| WO | 2006021528 | 3/2006 |
| WO | 2018160639 A1 | 9/2018 |
| WO | 2019110490 | 6/2019 |
| WO | 2020007356 | 1/2020 |
| WO | 2020007357 | 1/2020 |
| WO | 2020078916 | 4/2020 |
| WO | 2020208134 | 10/2020 |
| WO | 2021018422 | 2/2021 |
| WO | 2021030197 | 2/2021 |

OTHER PUBLICATIONS

S. Sadredding, Mirshafieyan, J. Guo, "Silicon colors: spectral selective perfect light absorption in single layer silicon films on aluminum surface and its thermal tunability," Optics Express. 22(25), 31545-315554 (2014).

T. Nagai et al., "Improvement of photoconductivity in Silicon Tin (SiSn) thin films," Journal of Non-Crystalline Solids 358 (2012) 2281-2284.

* cited by examiner

EFFECT PIGMENTS HAVING A REFLECTIVE CORE AND SEMICONDUCTOR LAYERS

The present invention relates to effect pigments having a reflective core. In general, effect pigments can be described as flake of platy structures that show light reflectance, scattering, absorption or an optically variable appearance that is dependent on the viewing direction to the substrate whereon or wherein these pigments are applied. Effect pigments are used for example in coatings for the automotive industry or in cosmetics.

Effect pigments are well known in the art and can generally be classified based on the core material for the flake of platy structure, which can be a metal or non-metal. Normally, this core material is coated with a number of different layers to provide for the desired optical effect.

In WO 1999/035194 thin metal effect pigments are disclosed comprising a thin reflector layer, typically a metal, with dielectric coatings disposed on the two opposing planar surfaces of thereof. Other layers can be added to this structure. Examples of suitable dielectric materials include silicon dioxide ($SiO_2$) and magnesium fluoride ($MgF_2$). However, the required thickness of the dielectric layers is >50 nm and the resulting chroma effect is low. Flakes will also exhibit color flop due to path-dependent interference effects. Moreover, all claimed layers adjacent to the metal core are dielectric layers having band gaps <3.5 eV and refractive indexes <2.0.

In US 2014/0368918 and US 2015/0309231 high chroma color pigments are disclosed in the form of a multilayer stack. US 2014/0368918 describes a pigment consisting of a minimum of a reflective core layer, a semiconductor absorber layer, a dielectric absorber layer but suggests additional dielectric and semiconductor layers for ideal chroma performance. US 20150309231 describes a pigment consisting of a minimum of a reflective core layer, a semiconductor absorber layer, a dielectric absorber layer and a high index of refraction dielectric layer. It is said that these type of pigments show a low red hue shift when viewed from a low angle (0°-45°). Such a hue shift will not be observed for the pigments disclosed in WO 1999/035194 using dielectric stacks as the adjacent material. In WO 2000/022418 a 7-layer pigment is described color-shifting dependent upon the angle of incidence of incoming light. The stack is described as a central reflective layer followed by isotropic selective absorbing, dielectric, and absorber layers. However, the structure of these pigments is quite complex and the manufacturing process is rather elaborate. Furthermore, the overall thicknesses of these effect pigments are quite high rendering the aspect ratios to be rather low which may cause problems of uniform plane-parallel orientation in the application media. This causes losses of gloss and chroma. The rather low content of opaque metal in these effect pigments is quite low which diminishes the hiding power.

There is a need for effect pigments having appealing optical properties like color, flop and high gloss combined with high hiding power but having a simple structure. Especially there is a need for effect pigments which additionally have a deep blue or green interference color.

Another object is to provide a process to manufacture such effect pigment.

The object is solved by providing an effect pigment having a layer stack which comprises a metallic flake having a first major interface and opposed to this first interface a second major interface, and at least one side surface and directly adjacent on one or of both of these major interfaces a semiconducting material having an average atomic composition of:
a) $Si_{(1-x)}Sn_x$, wherein $0<x<0.90$ or
b) $Ge_{(1-y)}Sn_y$, wherein $0<y\leq0.80$ or
c) $Si_{(1-m-n)}Ge_mSn_n$, wherein $0<m<1.00$, $0<n<1.00$ and with the proviso that $m+n<1.00$.

Further preferred embodiments to this effect pigment include effect pigments, wherein the highly reflective metallic flake is coated on both major interfaces with the semiconductor material and wherein additionally the semiconductor layers are coated with further dielectric, reflective or absorbing materials.

A further particularly preferred embodiment is directed to an effect pigment wherein the layer stack consists of the metallic flake having a first major interface and opposed to this first interface a second major interface, and at least one side surface and directly adjacent on both of these major interfaces a semiconducting material having an average atomic composition of:
a) $Si_{(1-x)}Sn_x$, wherein $0<x<0.90$ or
b) $Ge_{(1-y)}Sn_y$, wherein $0<y\leq0.80$ or
c) $Si_{(1-m-n)}Ge_mSn_n$, wherein $0<m<1.00$, $0<n<1.00$ and with the proviso that $m+n<1.00$.

Further preferred embodiments of the effect pigments are disclosed claims 4 to 11.

A further object of the invention was solved by providing a method of manufacturing the effect pigment using a PVD process comprising the steps:
a) coating a thin, flexible substrate with a release coat agent,
b) depositing semiconductor layer 1 onto the flexible substrate using a roll-to-roll process,
c) depositing a layer of a reflective metal onto the semiconductor layer 1,
d) depositing a second semiconductor layer 2 onto the reflective metal layer,
e) stripping the material stack from the flexible substrate in a solvent and
f) optionally further steps including particle sizing, particle classification and solvent dispersion.

Further preferred embodiments of this process are disclosed in claims 13 and 14.

A particularly favourable property of the thin effect pigments according to the present invention is an exceptionally high flop index in comparison to known high flop index pigments such as Metalure Liquid Black. The flop index is a measurement of the change in reflectance of a metallic color as it is rotated through the range of viewing angles. The effect pigment according to the present invention can have a flop index above 25, more particularly a flop index above 30. The effect pigment according to the present invention can have a flop index in the range of 25 to 250, more in particular a flop index in the range of 30 to 200 and preferably 35 to 200.

In addition, unlike many interference-based pigments, the effect pigments according to the three-layered embodiment show little color shifting as a function of viewing angle.

Within this invention the term "a highly reflective metallic flake" denotes to a platy metal particle with an essentially flat surface is meant. Such metal flakes reflect electromagnetic radiation of optical wavelength in a high amount without much scattering. These flat metal flakes may also be contrasted to metal substrates having diffractive structures such as embossed structures leading to diffraction phenomena.

In a further embodiment, the highly reflective metal is selected from the group consisting of aluminum, copper, chromium, titanium, zinc, silver, gold and alloys thereof.

Preferably the highly reflective material is aluminum which includes also alloys based on aluminum.

In further embodiments the semiconductor material has a bandgap in the range of 0.1 to 2.5 eV and further preferred in a range of 0.2 to 1.5 eV, in a more preferred embodiment the bandgap is in a range of 0.3 to 1.4 eV and in the most preferred embodiment the bandgap is in a range of 0.4 to 1.2 eV.

Preferably the semiconductor material is selected from average atomic compositions of a) $Si_{(1-x)}Sn_x$, wherein $0.02 \leq x \leq 0.75$ or
b) $Ge_{(1-y)}Sn_y$, wherein $0.02 \leq y \leq 0.60$ or
$Si_{(1-m-n)}Ge_mSn_n$, wherein $0.02 \leq m \leq 0.8$, $0.02 \leq n \leq 0.75$ with the proviso that m+n<1.00.

In further preferred embodiments of the effect pigment the semiconducting material has average atomic compositions of:

a) $Si_{(1-x)}Sn_x$, wherein $0.05 \leq x \leq 0.55$ or
b) $Ge_{(1-y)}Sn_y$, wherein $0.05 \leq y \leq 0.50$ or
c) $Si_{(1-m-n)}Ge_mSn_n$, wherein $0.05 \leq m \leq 0.65$, $0.05 \leq n \leq 0.55$ with the proviso that m+n<1.00.

The x, y, n and m are mole fractions. These materials are alloys of silicon and germanium with tin, respectively. Germanium adds interesting color effects as this material is absorbing in the visible wavelength region. Due to the high costs of this material the content of germanium is preferably as low as possible.

The molar amounts of the metals are preferably detected by ICP-OES (Inductively Coupled Plasma combined with Optical Emission Spectroscopy) after dissolving the whole effect pigments in acidic solutions. Another possible detection method is energy dispersive X-ray spectroscopy (EDX).

The effect pigment according to the present invention can be represented as a multilayer setup A-B, A-B-A or an A-B-C system, with B being a highly reflective material and adjacent layer A and C a semiconductor material having a bandgap of 0.1 to 2.5 eV.

The highly reflective material B is normally a flake or platy material having a mean thickness in the range from 5 to 500 nm, more preferably in the range from 5 to less than 100 nm, even more preferably in the range from 7 to less than 75 nm and most preferably in the range from 10 to 50 nm.

For the purposes of the present invention, the mean thickness of the platy metal material as well as the thickness of the semiconductor layers are determined by means of a SEM (Scanning Electron Microscope). Here a cross section a prepared preferably by incorporating the effect pigments in a concentration of about 10 wt. % into a two-component clearcoat (e.g. Auto-clear Plus HS from Sikkens GmbH) with a sleeved brush, applied to a film with the aid of a spiral applicator (wet film thickness 26 µm), dried and cut into cross section. Using this method, the cross section of an adequate number of particles should be measured so as to realize a representative statistical evaluation. Customarily, approximately 50 to 100 particles are measured.

The effect pigment according to the present invention may consist of only two or three layers, as reflected above, as a multilayer setup A-B or an A-B-C system, with B being a highly reflective material and adjacent layer A and C a semiconductor material having a bandgap of 0.1 to 2.5 eV. Such layers are optically active within the visible wavelength region. Three-layered effect pigments are most preferred as they exhibit an essentially uniform color impression when applied in a suitable media.

If both adjacent A and C layers are present, they can be of the same material leading to a A-B-A layer stack or different. Preferably A and C layers are of the same material. The mean thickness of layers A and C can be the same or different. Typically, the mean thickness of layers A and C can be in the range of 5-200 nm. Ideally the thickness is <200 nm, more ideally the thickness is <100 nm, and most ideally, the thickness is <75 nm.

A preferred mean thickness of layers A and/or C is in a range of 7 to 100 nm and more preferred in a region of 10 to 35 nm.

In further preferred embodiments the total average thickness of the effect pigment (meaning the sum of layers A, B and C) is in a range of 35 to below 300 nm, more preferred in a range of 50 to below 250 nm and most preferred in a range of 70 to below of 200 nm. Such effect pigments have a rather low total thickness leading to a high aspect ratio which favours plane-parallel orientation when the effect pigment is applied from a wet coating formulation on a substrate. A high plane-parallel orientation in turn will enhance the gloss, brightness and flop. Additionally, these effect pigments have a rather high content of the central metal layer leading to a very well hiding power.

For these preferred embodiments with restricted total average thicknesses the semiconductor layers A and C preferably independently have an average thickness in the range of 7 to 60 nm, more preferably in a range of 10 to 50 nm and most preferably in a range of 10 to 35 nm.

Within the scope of the present invention, a dielectric material is an insulator (a poor electrical conductor), such as ceramics, diamond, etc., that typically has a bandgap in excess of ~4 eV. These dielectric materials are typically optically transparent; i.e. they have very poor absorption in the visible region of the electromagnetic spectrum.

In a very preferred embodiment the effect pigment the flake of a highly reflective material is made from aluminum and the semiconductor material is an alloy of silicon and tin or germanium and tin and most preferred a silicon-tin alloy.

Most preferred is an effect pigment having and A-B-A layer stack, wherein the central layer B is aluminum and the adjacent layers A are a silicon-tin alloy or a germanium-tin alloy and most preferred a silicon-tin alloy.

The color and other optical properties of the effect pigment according to the present invention can be made visible and measurable by incorporating the effect pigment in a colorless binder system and by using the obtained composition to coat a substrate. For example, an ink-composition can be obtained by mixing about 6 wt. % of the effect pigment according to the present invention with a colorless nitrocellulose binder and preparing a drawdown on a sample card, for example a BYK Gardner drawdown card.

The optical properties of the material on the drawdown card can be measured using a BYK-mac i MetallicColor.

In general it was found that for the effect pigments according to the present invention, the color of the pigment shifts from the reddish part of the color spectrum to the blueish part by increasing the layer thickness of the semiconducting material deposited on the highly reflective material. A similar effect was found by holding the layer thickness of a semiconducting material constant and replacing the semiconducting material with one of a higher refractive index.

Regarding the sizes and size distributions of the diffractive flaky effect pigments typical size ranges of printing inks or cosmetic formulations are chosen. Preferably the flaky effect pigment have a $d_{50}$ of the particle size distribution is in a range of 2 to 100 μm, more preferably in a range of 5 to 45 μm, furthermore preferred in a range of 6 to 35 μm and most preferably in a range of 7 to 30 μm.

The pigment size is typically indicated using quantiles (d values) from the volume averaged particle size distribution. Here, the number indicates the percentage of particles smaller than a specified size contained in a volume-averaged particle size distribution. For example, the $d_{50}$ value indicates the size where 50% of the particles are smaller than this value. These measurements are conducted e.g. by means of laser granulometry using a particle size analyzer manufactured by Horiba and is a Horiba LA 950 instrument. The measurements are conducted using Fraunhofer approximation and suitable parameters according to information from the manufacturer.

The $d_{10}$-values characterize the amount of fine particles and typically range from 2 to 20 μm and preferably from 4 to 15 μm.

The $d_{80}$-values characterize the amount of coarse particles and typically range from 15 μm to 140 μm and preferably from 20 μm to 50 μm.

The width of the particle size distribution can be characterized by the span defined as $(d_{90}-d_{10})/d_{50}$ and preferably this span is in a range of 1.50 to 2.2 and more preferably in a range of 1.6 to 2.0.

In certain embodiments the effect pigments might be encapsulated with a further outer layer. Such encapsulation might be necessary to ensure gassing stability for water-based coating systems or water-based printing inks, for example. As the edges of the flaky metal are not covered by the semiconductor layers the effect pigment can be particularly attacked by a corrosive media such as a water-based coating formulation.

Typically these encapsulating layers will be used in an amount of and from materials which effectively protect the effect pigment from corrosion but at the same time do not alter the optical appearance too much. Typically materials of low refractive index are used and typically the materials are not colored or when they are colored, they are used in very small amounts. Therefore, the enveloping layer is of an essentially optically non-active material.

In preferred embodiments the further layer encapsulates essentially the whole effect pigment and consists of a layer of Mo-oxide, $SiO_2$, $Al_2O_3$, or surface modifiers like organofunctional silanes, phosphate ester, phosphonate esters, phosphite esters and combinations thereof.

More preferably the optically further layer encapsulates the whole effect pigment and consists of a layer of Mo-oxide, $SiO_2$ and optionally a surface modifier like organofunctional silanes. Such systems are described e.g. in WO 2019/110490 A1. In another preferred embodiment the optically non-active layer consists of a layer of $SiO_2$ and optionally a further layer of organofunctional silanes which serve as modifier agents of the $SiO_2$ surface.

The organofunctional silanes are primarily needed as surface modifiers here to adjust the chemical compatibility of the effect pigment to the binder medium of the final application as described in e.g. EP 1084198 A1.

The organofunctional silanes used preferably as surface modifiers, which contain suitable functional groups, are available commercially and are produced, for example, by Evonik, Rheinfelden, Germany and sold under the trade name "Dynasylan®". Further products can be purchased from OSi Specialties (Silquest® silanes) or from Wacker (Genosil® silanes).

Examples of suitable organofunctional silanes are 3-methacryloxypropyl trimethoxy silane (Dynasylan MEMO), vinyl tri(m)ethoxy silane (Dynasylan VTMO or VTEO), 3-mercaptopropyl tri(m)ethoxy silane (Dynasylan MTMO or 3201), 3-glycidyloxypropyl trimethoxy silane (Dynasylan GLYMO), tris(3-trimethoxysilylpropyl) isocyanurate (Silquest Y-11597), gamma-mercaptopropyl trimethoxy silane (Silquest A-189), bis(3-triethoxysilylpropyl) polysulfide (Silquest A-1289), bis(3-triethoxysilyl) disulfide (Silquest A-1589), beta(3,4-epoxycyclohexyl) ethyl-tri-methoxysilane (Silquest A-186), gamma-isocyanatopropyl-trimethoxsilane (Silquest A-Link 35, Genosil GF40), (methacryloyloxymethyl) trimethoxysilane (Genosil XL 33) and (isocyanatomethyl) trimethoxysilane (Genosil XL 43).

In one preferred embodiment the organofunctional silane mixture that modifies the $SiO_2$ layer comprises at least one amino-functional silane. The amino function is a functional group which is able to enter into chemical interactions with the majority of groups present in binders. This interaction may involve a covalent bond, such as with isocyanate or carboxylate functions of the binder, for example, or hydrogen bonds such as with OH or COOR functions, or else ionic interactions. It is therefore very highly suitable for the purpose of the chemical attachment of the effect pigment to different kinds of binder.

The following compounds are employed preferably for this purpose: aminopropyl trimethoxy silane (Dynasylan AMMO), aminopropyl triethoxy silane (Dynasylan AMEO), N-(2-aminoethyl)-3-aminopropyl trimethoxy silane (Dynasylan DAMO), N-(2-aminoethyl)-3-aminopropyl triethoxy silane, triamino-functional trimethoxy silane (Silquest A-1130), bis(gamma-trimethoxysilylpropyl)amine (Silquest A-1170), N-ethyl-gamma-aminoisobutyl trimethoxy silane (Silquest A-Link 15), N-phenyl-gamma-diaminopropyl trimethoxy silane (Silquest Y-9669), 4-amino-3,3-dimethyl-butyltrimethoxy-silane (Silquest Y-11637), (N-cyclohexylaminomethyl)-triethoxy silane (Genosil XL 926), (N-phenylaminomethyl)-trimethoxy silane (Genosil XL 973) and mixtures thereof.

In another embodiment pre-hydrolysed and pre-condensated organofunctional silanes may be used as described in EP 3080209 B1.

In other embodiments the further encapsulating is based on $SiO_2$ which is further modified by organofunctional silanes to produce a hybrid inorganic/organic layer. Such modifying organofunctional silanes may be a diphenyl dimethoxy silane, a diphenyl diethoxy silane, an amino silane and the like.

In other embodiments the encapsulating optically non-active layer is based on $SiO_2$ as inorganic component and layers comprising organic oligomers or polymers are formed as described in WO 2007/017195 A2 or in WO 2016/120015 A1.

In other embodiments the organofunctional silanes or other corrosion inhibitors like phosphate ester, phosphonate esters, phosphite esters and combinations thereof may be coated directly on the effect pigment to impart corrosion and gassing stability especially to the edges of the effect pigment.

The effect pigments according to the present invention can be manufactured using a physical vapor deposition (PVD) process. In such method of manufacturing the effect pigment, using a PVD process comprises the steps:

a) coating a thin, flexible substrate with a release coat agent, b) depositing a first semiconductor layer onto the flexible substrate using a roll-to-roll process,
c) depositing a layer of a highly reflective metal onto the first semiconductor layer,
d) depositing a second semiconductor layer onto the highly reflective metal layer,
e) stripping the material stack from the flexible substrate in a solvent and
f) optionally further steps including particle sizing, particle classification and solvent dispersion.

The release coat step may be skipped if a metallized film is to be produced without intention of stripping the stack material.

The above process produces a material stack that may be stripped from the flexible substrate in a subsequent step. The above process may be mirrored on the opposing side of the film, and multiple stacks may be deposited on a single film by repeating the process. Additionally, a single side may be colored with the opposing side maintaining the metal optical properties by removing one of the semiconductor layers. If the first semiconductor layer is removed, the metal side will be colored, while if the second semiconductor layer is removed, the web-side will be colored.

In the case of pigment manufacturing, the material deposited from the abovementioned substrate is typically stripped utilizing a solvent or mechanical stripping process, followed by post processing steps, which may include particle sizing, particle classification, and solvent dispersion.

In preferred embodiments highly reflective metal film has a thickness in a range of 5 to 500 nm.

All materials for the reflective metal, the semiconductor layer and the thicknesses of these layers can be the same as previously disclosed.

Step a): This step is conducted essentially in the same manner than known from the manufacture of PVD metal pigments, especially aluminum effect pigments. The flexible substrate is usually a web made from polymers and most preferably a PET polymer. As release agents those common in the art can be used. Usually the release agents are polymers like for example acrylics, methacrylics or polystyrol. They can be also other organic materials as described in US 2004/0131776 A1 or in US 20100062244 A1.

In steps b) and d) in one embodiment semiconductor alloys of a predetermined composition are independently used as bulk materials which are evaporated by suitable means to produce respective gas molecules which are transferred to the flexible substrate coated with a release layer under ultra-high vacuum conditions.

In another embodiment two or three suitable bulk semiconductor materials of a predetermined purity are used wherein their vapor clouds are allowed to overlap before reaching the substrate.

Steps b) to d) can be conducted as an electron beam process, magneton sputtering, resistive evaporation or inductive heating. Most preferred is evaporation of the semiconductor bulk material by an electron beam process.

Steps e) and f) are again well known in the art. Preferred solvents for stripping of the material stack from the flexible substrate in step e) are acetone, ethyl acetate, propylene glycol methoxy ether, isopropyl alcohol, ethanol, or water.

In further preferred embodiments the first semiconductor layer and the second semiconductor layer are composed of the same material.

In further preferred embodiments the first and the second semiconductor layers essentially have the same thickness. With "essentially have the same thickness" it is meant that the deviations of the thickness of the first and the second semiconductor layers are less than 15%. If additionally the first and second semiconductor layer are made from the same material the coloration on will be the same on both sides of the reflective metal.

The effect pigments according to the present invention can be used in a broad range of applications, typically for metallic effect pigments, such as coatings, printing inks, cosmetic formulations or plastics.

Another embodiment of the present invention is concerned with a coating system comprising a binder and the flaky effect pigments of this invention. The binder systems can be acrylics, polyesters, polyurethanes, polyepoxides and copolymers from these. Preferably the coating systems are automotive base coats.

Coating or ink compositions comprising these effect pigments can show a very high flop index, for example a flop index in the range of 20-200 or preferably in the range of 25 to 200.

A further aspect of this invention is directed to a coating composition, an ink composition, a cosmetic formulation or a plastic comprising an effect pigment described herein.

Some further aspects of this invention relate to a coated film of the material stacks described before. Such films can be regarded as precursor materials for the manufacture of the final effect pigments.

Aspect 1 relates to a film coated on a flexible substrate with a first layer of a semiconductor having an average atomic composition of:
  a) $Si_{(1-x)}Sn_x$, wherein $0<x<0.90$ or
  b) $Ge_{(1-y)}Sn_y$, wherein $0<y\leq 0.80$ or
  c) $Si_{(1-m-n)}Ge_mSn_n$, wherein $0<m<1.00$, $0<n<1.00$ with the proviso that $m+n<1.00$
and a layer of a highly reflective metal coated thereon.

Aspect 2 relates to aspect 1, wherein a further layer of semiconductor material having independently from the first semiconductor layer an average atomic composition of:
  a) $Si_{(1-x)}Sn_x$, wherein $0<x<0.90$ or
  b) $Ge_{(1-y)}Sn_y$, wherein $0<y\leq 0.60$ or
  c) $Si_{(1-m-n)}Ge_mSn_n$, wherein $0<m<1.00$, $0<n<1.00$ with the proviso that $m+n<1.00$
is coated on the layer of a highly reflective metal.

Aspect 3 relates to aspects 1 or 2, wherein the highly reflective metal is selected from the group consisting of aluminum, copper, chromium, titanium, zinc, silver, gold and alloys thereof.

Aspect 4 relates to any of the preceding aspects, wherein the flake of a highly reflective material has an average thickness in the range from 5 to 500 nm.

Aspect 5 relates to any of the preceding aspects, wherein the layer of the semiconductor material has a mean thickness in the range from 5 to 200 nm.

All further embodiments disclosed in this invention with respect to the effect pigments (except the encapsulating layer with optically non-active layers and the surface modification coatings) do equally apply to the film stacks covered by the before-mentioned aspects.

EXAMPLES

Example 1a, and 1b

3-Layer Material (SiSn—Al—SiSn,)

A layer of Si—Sn alloy (solid solution, Sn a solute) was deposited on a 30 cm wide clear polyester film coated with a CAB (Cellulose Acetate Butyrate) based release agent using e-beam PVD evaporation. A second discrete layer of Al was deposited onto the Si—Sn alloy using same system with targeted optical density of approximately 1.0-1.5 OD. 3-layer materials were prepared after the deposition of third discrete layer of Si and Sn alloy, where optical densities of each layer are approximately 0.5-0.7 OD for 1a, and 0.4-0.6 OD for 1b, onto the Al layer in the similar condition of the first layer. In each process, the e-beam source was positioned 36 cm below the film. The e-beam source accelerating voltage was held at a constant 10 kV throughout the run.

In the alloy deposition steps, the first Si—Sn alloy-layer was deposited on the CAB side of a clear polyester film (web) using PVD e-beam evaporation. In-situ optical transmission sensors were utilized to determine the alloy thickness, and e-beam current and web-speed was manipulated to target the appropriate layer thickness. The third layers was performed in the similar condition after the Al deposition.

The thickness of the two Si—Sn layers was targeted to be the same, so that the web-side and metal side of each condition would be the same color. Silver-green (Ex. 1a) and blue (Ex. 1b) color tones were each targeted and successfully produced. The coloration of the web and metal side of the films matched well in each material set. The coloration of the web and metal side of the films matched well in each material set.

In the second step, an Al layer was deposited corresponding to approximately targeted optical density. Optical transmission sensors in combination with current adjustment was utilized to target appropriate Al thickness.

The average SiSn and Al layer thickness for Example 1a, obtained via SEM analysis, is 57+/−3 nm and 18+/−3 nm with a silicon: tin atomic ratio determined from energy dispersive spectroscopy of 82:18. The average SiSn and Al layer thickness for Example 1b, obtained via SEM analysis, is 47+/−3 nm and 18+/−3 nm with a silicon: tin atomic ratio determined from energy dispersive X-ray spectroscopy of 82:18.

Example 2:3-Layer Material (GeSn—Al—GeSn,)

As the process was described in example 1, A layer of Ge—Sn alloy (solid solution, Sn a solute) was deposited on a 30 cm wide clear polyester film coated with a CAB (Cellulose Acetate Butyrate) based release agent using e-beam PVD evaporation for example 2. A second discrete layer of Al was deposited onto the Ge—Sn alloy using same system with targeted optical density of approximately 1.0-1.5 OD. 3-layer materials were prepared after the deposition of third discrete layer of Ge and Sn alloy with optical density that is approximately 0.5-0.75 OD, onto the Al layer in the similar condition of the first layer. In each process, the e-beam source was positioned 36 cm below the film. The e-beam source accelerating voltage was held at a constant 10 kV throughout the run.

In the alloy deposition steps, the first Ge—Sn alloy-layer was deposited on the CAB side of a clear polyester film (web) using PVD e-beam evaporation. In-situ optical transmission sensors were utilized to determine the alloy thickness, and e-beam current and web-speed was manipulated to target the appropriate layer thickness. The third layers was performed in the similar condition after the Al deposition.

The thickness of the two Ge—Sn layers was targeted to be the same, so that the web-side and metal side of each condition would be the same color. A blue color tone was targeted and successfully produced. The coloration of the web and metal side of the films matched well in this material set.

In the second step, an Al layer was deposited corresponding to approximately targeted optical density. Optical transmission sensors in combination with current adjustment was utilized to target appropriate Al thickness.

The average GeSn and Al layer thickness for Example 2, obtained via SEM analysis, is 25+/−3 nm and 20+/−3 nm with a germanium: tin atomic ratio determined from energy dispersive X-ray spectroscopy of 80:20.

The materials obtained in Example 1a, and 1b, and 2 were all stripped from the polyester film and milled/crushed to a particles size listed in Table 1 (D50 value). Pigments were prepared with a 25 wt. % in ethanol. Inks were prepared a binder system, composed of Hagedorn H7 Nitrocellulose binder (obtainable from Hagedorn AG, Osnabrück, Germany) in a solvent blend of ethyl acetate and propylene glycol monomethyl ether. Formulations were based on weight ratios of metals content to binder, with a binder-to-pigment weight ratio of 31:69. The samples were drawn down on a flat BYK drawdown card at a wet-film thickness of 40 μm. Gloss data were collected using a BYK Micro Tri-gloss meter. Additional optical data were collected using a BYK Mac meter. The results of these measurements are summarised in Table 1.

TABLE 1

Optical data of Examples

| Sample | Particle Size D50 (μm) | Flop Index | $L^*_{(-15°)}$ (trans) | $L^*_{15°}$ | $L^*_{45°}$ | $a^*_{15°}$ | $b^*_{15°}$ | Visual color |
|---|---|---|---|---|---|---|---|---|
| Ex. 1a | 15.7 | 41 | 131 | 110 | 18 | −4.5 | 4.9 | Silvery green |
| Ex. 1b | 15.1 | 36 | 111 | 94 | 17 | −5 | −13 | Teal blue |
| Ex. 2 | 14.1 | 25 | 110 | 91 | 24 | −5.7 | −15 | Teal blue |

The invention claimed is:

1. An effect pigment having a layer stack which comprises a highly reflective metallic flake having a first major interface and opposed to this first interface a second major interface, and at least one side surface and directly adjacent on one or of both of these major interfaces a layer of a semiconducting material having an average atomic composition of:
   a) $Si_{(1-x)}Sn_x$, wherein $0<x<0.90$ or
   b) $Ge_{(1-y)}Sn_y$, wherein $0<y\leq0.80$ or
   c) $Si_{(1-m-n)}Ge_mSn_n$, wherein $0<m<1.00$, $0<n<1.00$ and with the proviso that $m+n<1.00$.

2. An effect pigment according to claim 1, wherein the highly reflective metallic flake is coated on both major interfaces with the semiconductor material and wherein additionally the semiconductor layers are coated with further dielectric, reflective or absorbing materials.

3. An effect pigment according to claim 1, wherein the layer stack consists of the highly reflective metallic flake having a first major interface and opposed to this first interface a second major interface, and at least one side surface and directly adjacent on both of these major interfaces a layer of a semiconducting material having an average atomic composition of:
   a) $Si_{(1-x)}Sn_x$, wherein $0<x<0.90$ or
   b) $Ge_{(1-y)}Sn_y$, wherein $0<y\leq0.80$ or
   c) $Si_{(1-m-n)}Ge_mSn_n$, wherein $0<m<1.00$, $0<n<1.00$ and with the proviso that $m+n<1.00$.

4. The effect pigment of claim 1, wherein the semiconducting layer or layers have a bandgap in a range of 0.1 to 2.5 eV.

5. The effect pigment of claim 1, wherein the highly reflective metal flake is selected from the group consisting of aluminum, copper, chromium, titanium, zinc, silver, gold or alloys thereof.

6. The effect pigment according to claim 1, wherein the average atomic composition of the semiconducting material is:
   a) $Si_{(1-x)}Sn_x$, wherein $0.02 \leq x \leq 0.75$ or
   b) $Ge_{(1-y)}Sn_y$, wherein $0.02 \leq y \leq 0.60$ or
   c) $Si_{(1-m-n)}Ge_mSn_n$, wherein $0.02 \leq m \leq 0.8$ and $0.02 \leq n \leq 0.75$.

7. A flaky effect pigment according to claim 1, wherein the average atomic composition of the semiconducting material is:
   a) $Si_{(1-x)}Sn_x$, wherein $0.05 \leq x \leq 0.55$ or
   b) $Ge_{(1-y)}Sn_y$, wherein $0.05 \leq y \leq 0.50$ or
   c) $Si_{(1-m-n)}Ge_mSn_n$, wherein $0.05 \leq m \leq 0.65$ and $0.05 \leq n \leq 0.55$.

8. The effect pigment according to claim 1, wherein the highly reflective metallic flake has an average thickness in the range from 5 to 500 nm.

9. The effect pigment according to claim 1, wherein the layer of the semiconductor material has a mean thickness in the range from 5 to 200 nm.

10. The effect pigment according to claim 1, wherein the effect pigment is further encapsulated with an outer layer.

11. The effect pigment according to claim 10, wherein the further encapsulating layer consists of a layer of Mo-oxide, $SiO_2$, $Al_2O_3$ or a surface modifier.

12. The effect pigment according to claim 11, wherein the further encapsulating layer consists of a surface modifier, the surface modifier comprising one or more of an organofunctional silane, a phosphate ester, a phosphonate esters, and a phosphite esters.

13. An ink composition comprising the effect pigment of claim 1 and a binder.

14. A product comprising the effect pigment of claim 1 in the form of a cosmetic composition.

15. A composition comprising a plastic and the effect pigment of claim 1.

16. A method of manufacturing an effect pigment using a PVD process comprising:
   a) coating a thin, flexible substrate with a release coat agent,
   b) depositing a first semiconductor layer onto the flexible substrate using a roll-to-roll process,
   c) depositing a layer of a highly reflective metal onto the first semiconductor layer,
   d) depositing a second semiconductor layer onto the highly reflective metal layer, and
   e) stripping the material stack from the flexible substrate in a solvent;
   the resulting effect pigment having a layer stack which comprises a highly reflective metallic flake having a first major interface and opposed to this first interface a second major interface, and at least one side surface and directly adjacent on one or of both of these major interfaces a layer of a semiconducting material having an average atomic composition of:
   a) $Si_{(1-x)}Sn_x$, wherein $0 < x < 0.90$ or
   b) $Ge_{(1-y)}Sn_y$, wherein $0 < y \leq 0.80$ or
   c) $Si_{(1-m-n)}Ge_mSn_n$, wherein $0 < m < 1.00$, $0 < n < 1.00$ and with the proviso that $m+n < 1.00$.

17. The method of manufacturing according to claim 16, wherein the highly reflective metal has a thickness in a range of 5 to 500 nm.

18. The method of manufacturing according to claim 16, wherein the first semiconductor layer and the second semiconductor layer are composed of the same material.

19. The method of claim 16, further comprising one or more steps of particle sizing, particle classification and solvent dispersion.

* * * * *